(12) United States Patent
Palmer et al.

(10) Patent No.: US 9,841,897 B2
(45) Date of Patent: Dec. 12, 2017

(54) DEVICES, METHODS AND SYSTEMS FOR ASSESSMENT AND RECORDATION OF REACTIONS TO STIMULI

(71) Applicant: OPERTECH BIO, INC., Philadelphia, PA (US)

(72) Inventors: R. Kyle Palmer, Cranbury, NJ (US); Daniel J. Long, Philadelphia, PA (US)

(73) Assignee: Opertech Bio, Inc., Philadelphia, PA (US)

( * ) Notice: Subject to any disclaimer, the term of this patent is extended or adjusted under 35 U.S.C. 154(b) by 0 days.

(21) Appl. No.: 15/017,294

(22) Filed: Feb. 5, 2016

(65) Prior Publication Data

US 2016/0154581 A1 Jun. 2, 2016

Related U.S. Application Data

(63) Continuation of application No. PCT/US2014/050155, filed on Aug. 7, 2014.

(60) Provisional application No. 61/863,242, filed on Aug. 7, 2013.

(51) Int. Cl.
```
G09B 19/00      (2006.01)
G06F 3/0488     (2013.01)
G06Q 30/02      (2012.01)
A61B 5/00       (2006.01)
```

(52) U.S. Cl.
CPC ........ *G06F 3/04886* (2013.01); *A61B 5/4017* (2013.01); *A61B 5/7246* (2013.01); *G06Q 30/0201* (2013.01); *A61B 5/7475* (2013.01)

(58) Field of Classification Search
CPC ............ G06Q 30/0201; G06F 3/04886; A61B 5/4017

USPC .......................................... 434/127; 73/865.7
See application file for complete search history.

(56) References Cited

U.S. PATENT DOCUMENTS

| | | | |
|---|---|---|---|
| 4,940,056 A * | 7/1990 | Heck .................. | A61B 5/04085 600/373 |
| 6,062,277 A | 5/2000 | Seo | |
| 8,364,520 B1 * | 1/2013 | Eichorn ................ | G06Q 30/02 705/7.31 |
| 2002/0177756 A1 * | 11/2002 | Pierre Godinot ........ | A61B 5/00 600/300 |
| 2009/0281891 A1 | 11/2009 | Walker et al. | |

(Continued)

FOREIGN PATENT DOCUMENTS

EP          0845217          6/1998

OTHER PUBLICATIONS

Anonymous: "Automated pipetting system—Wikipedia", Mar. 22, 2013 (Mar. 22, 2013), XP055335599, Retrieved from the Internet: URL:https://en.wikipedia.org/w/index.php?title=Automated pipettingsystem&oldid=546409661.

(Continued)

*Primary Examiner* — Michael Grant
(74) *Attorney, Agent, or Firm* — Tyler J. Sisk; Casimir Jones, S.C.

(57) ABSTRACT

Provided herein are methods of recording objective responses of a subject to stimuli, and devices and user interfaces (UI) for use therewith. In particular, the present invention provides UIs that allow a user to record objective multivariable responses to stimuli, devices comprising such UIs, and methods of using such UIs and devices to assess the characteristics of a sample or product.

14 Claims, 6 Drawing Sheets

(56) References Cited

U.S. PATENT DOCUMENTS

| | | | |
|---|---|---|---|
| 2010/0025981 A1* | 2/2010 | Lay | G06T 11/206 283/115 |
| 2011/0038998 A1* | 2/2011 | Kohli | A47J 31/40 426/433 |
| 2013/0054383 A1* | 2/2013 | Holman | G06Q 10/10 705/15 |
| 2013/0065797 A1* | 3/2013 | Silbert | G01F 23/265 506/39 |
| 2014/0157133 A1* | 6/2014 | Li | G06Q 30/0201 715/738 |
| 2016/0353932 A1* | 12/2016 | Freas, II | A47J 43/04 |

OTHER PUBLICATIONS

Piero zucchelli: "The liquid handling robot using manual pipettes: Andrew.", youtube, Jun. 28, 2013 (Jun. 28, 2013), p. 1 pp., XP054977074, Retrieved from the Internet: URL:https://www.youtube.com/watch?v=IAM-wl1-15xWqdg.

Extended European Search Report dated Feb. 6, 2017 in corresponding European application No. 14834060.7.

* cited by examiner

DEVICES, METHODS AND SYSTEMS FOR ASSESSMENT AND RECORDATION OF REACTIONS TO STIMULI

CROSS-REFERENCE TO RELATED APPLICATIONS

The present application is a continuation of PCT Patent Application No. PCT/US2014/050155 filed 7 Aug. 2014, which claims the benefit of U.S. Provisional Application Ser. No. 61/863,242 filed 7 Aug. 2013, the entirety of each of which is herein incorporated by reference.

FIELD

Provided herein are methods of recording objective responses of a subject to stimuli, and devices and user interfaces (UI) for use therewith. In particular, the present invention provides UIs that allow a user to record objective multivariable responses to stimuli, devices comprising such UIs, and methods of using such UIs and devices to assess the characteristics of a sample or product.

BACKGROUND

When designing a product, or conducting market research, it is useful to gain an accurate and objective measure of the qualitative and/or quantitative reactions of a subject (e.g., a human subject) to a given product. For example, human taste testing is performed to obtain a measure of taste quality and/or palatability of test samples (e.g., foods, beverages, pharmaceuticals, nutriceuticals, etc.). Human taste testing typically requires large amounts of sample and large numbers of trained subjects in order to generate statistically relevant data. Testing conventionally uses 20-40 or more test subjects (e.g., human subjects) per test panel with each subject evaluating (e.g., consuming) a large amount of sample per analysis (e.g., 20, 30, 40 or more milliliters of sample solution). Therefore, generation of a working/testable amount of test sample needed for evaluation has remained a significant challenge. For example, a taste-active compound that is active in the mM range might need to be scaled to 10-100 s of grams for testing, which can be very costly, especially if the test article is a natural product. Human taste testing therefore remains time and resource intensive. Furthermore, due to predominant reliance on subjective verbal reports or rating scales for test measurement, human taste testing has been notoriously variable and inaccurate. Similar inefficiencies and inaccuracies exist for other types of human assessment testing as well.

Moreover, human taste testing has stagnated into a structure of testing and measurement that progressed from psychophysical methods originating over 100 years ago with little innovation since.

SUMMARY

Provided herein are methods of recording objective responses of a subject to stimuli, and devices and user interfaces (UI) for use therewith. In particular, the present invention provides UIs that allow a user to record objective multivariable responses to stimuli, devices comprising such UIs, and methods of using such UIs and devices to assess the characteristics of a sample or product. The present invention allows for improved accuracy and/or precision of testing, enables measurements to be achieved through objective means (not relying on verbal reports, rating scales, or subjective perceptions), and the accumulation of statistically relevant information from a small cohort of subjects (e.g., about 100, about 90, about 80, about 70, about 60, about 50, about 40, about 30, about 20, about 15, 14, 13, 12, 11, 10, 9, 8, 7, 6, 5, 4, 3, 2, 1, or ranges therein) using small amounts of test sample/compound (e.g., 2, 3, 4, 5, 6, 7, 8, 9, 10, 20, 30, 40, 50-70, 70-90, 100 or more fold less than the amount of test sample/compound conventionally used), and/or provides the capability of high throughput testing. In some embodiments, test samples are of an appropriate size for the particular sample (e.g., 50 µl, 100 µl, 150 µl, 200 µl, 250 µl, 300 µl, 350 µl, 400 µl, 450 µl, 500 µl, 600 µl, 700 µl, 800 µl, 900 µl, 1 ml, 1.5 ml, 2 ml, 2.5 ml, 3 ml, 3.5 ml, 4 ml, 4.5 ml, 5 ml, 6 ml, 7 ml, 8 ml, 9 ml, 10 ml, or more, or ranges or volumes therein.)

For example, in some embodiments, the present invention provides systems and/or devices for taste testing (e.g., human taste testing) comprising: (a) a touch screen; (b) an automated pipette component; and (c) a sample source. In some embodiments, the device further comprises a reward component (e.g., hopper). In some embodiments, the touch screen comprises a recordation grid. In some embodiments, the recordation grid is displayed on the touch screen. In some embodiments, the recordation grid is not viewable on the touch screen. In some embodiments, a first dimension of the grid corresponds to a first taste-testing characteristic and a second dimension of the grid corresponds to a second taste-testing characteristic. The invention is not limited by the number of sample characteristics measured and/or dimensions integrated into the grid (or matrix). Indeed, the grid (or matrix) may comprise, 2, 3, 4, 5, 6, 7 or more dimensions (e.g., with each dimension corresponding to or correlating with a characteristic of the sample). In some embodiments, the first taste-testing characteristic is palatability and the second taste-testing characteristic is taste quality. In some embodiments, the automated pipette component is configured to withdraw a sample from the sample source and to deliver the sample to a test subject. In some embodiments, the automated pipette component is configured to deliver sample to a test subject positioned in front of the touch screen. In some embodiments, a device further comprises a processor component and a memory component. In some embodiments, the processor directs the automated pipette component to deliver a first sample from the sample source to a test subject. In some embodiments, the processor identifies contact of the touch screen by the test subject as a taste-test response. In some embodiments, the taste-test response is recorded in the memory and correlated to the first sample. In some embodiments, sample delivery, contact identification, recordation, and correlation are repeated for one or more additional samples (e.g., $2^{nd}$ sample, $3^{rd}$ sample ... $10^{th}$ sample ... $50^{th}$ sample ... $100^{th}$ sample, or more). In some embodiments, the sample source is a microtiter plate. The invention is not limited by the number of samples or by the type of plate used to house the samples. For example, in some embodiments, the microtiter plate is a 6-, 8-, 12-, 16-, 24-, 32-, 58-, 64-, 96-, 384- or more well plate comprising 6, 8, 12, 16, 24, 32, 48, 64, 96, 384, or more different samples. In some embodiments, the sample source comprises one or more vials, tubs, cups, tubes, channels, microfluidic channels, plates, etc. The device may further comprise wireless capabilities that transmits taste-test responses over a wireless network to a remote storage component. Data present in memory component and/or the remote storage component may be accessed and analyzed at any time after testing has been completed.

In certain embodiments, the present invention provides systems for taste testing (e.g., human taste testing) comprising: (a) a recordation component; and (b) a sample delivery component. The recordation component may be electronic (e.g., digital (e.g., touch screen) or analog) or manual (e.g., paper or other markable material). In some embodiments, the recordation component comprises a recordation grid. The grid may be viewable by a subject or virtual (e.g., not readily visible). In some embodiments, a first dimension of the grid corresponds to a first taste-testing characteristic and a second dimension of the grid corresponds to a second taste-testing characteristic. The invention is not limited by the number of sample characteristics measured and/or dimensions integrated into the grid (or matrix). Indeed, the grid (or matrix) may comprise, 2, 3, 4, 5, 6, 7 or more dimensions (e.g., with each dimension corresponding to or correlating with a characteristic of the sample). In some embodiments, the first taste-testing characteristic is palatability and the second taste-testing characteristic is taste quality. In some embodiments, the sample delivery component is configured to provide a test subject with sample. A sample delivery component may be a delivery pipette, a straw, cup, tube, glass, syringe, card, channel, etc. In some embodiments, a test subject manually selects the delivery component and obtains the sample. In other embodiments, the delivery component automatically provides the test subject with a sample. In some embodiments, an automated delivery component is configured to deliver sample to a test subject positioned in front of the recordation component. In some embodiments, the delivery component transfers sample from a sample source to a test subject. In some embodiments, a processor directs the automated delivery component to deliver a first sample from the sample source to a test subject. In some embodiments, the processor identifies contact of the recordation component by the test subject as a taste-test response. In some embodiments, the taste-test response is recorded in a memory component and correlated to the first sample. In some embodiments, sample delivery, contact identification, recordation, and correlation are repeated for one or more additional samples (e.g., $2^{nd}$ sample, $3^{rd}$ sample . . . $10^{th}$ sample . . . $50^{th}$ sample . . . $100^{th}$ sample, or more). In some embodiments, the sample source is a microtiter plate; a series of vials, cups, wells, tubes, etc.; a microfluidic device; etc. In some embodiments, a sample source comprises a single vessel, well, container, etc. for each test sample to be given to a subject (e.g., each vessel, well, container, etc. is accessed only once). In some embodiments, a sample source comprises one vessel, well, container, etc. for each type of sample to be given to a subject (e.g., the vessel, well, container, etc. is re-accessed for repeat trials). The invention is not limited by the number of samples or by the type of source used to house the samples. For example, in some embodiments, the sample source is a 6-, 8-, 12-, 16-, 24-, 32-, 48-, 64-, 96-, 384- or more well plate comprising 6, 8, 12, 16, 24, 32, 48, 64, 96, 384, or more different samples (or ranges therein). A system may further comprise wired and/or wireless capabilities to transmit test responses over a network (e.g., wireless network) to a remote storage component (e.g., a data server). Data present in memory component and/or the remote storage component may be accessed and analyzed at any time after testing has been completed.

In some embodiments, the present invention provides methods of conducting human sample testing (e.g., taste testing) comprising: (a) delivering a sample from a sample source to a subject positioned in front of a recordation component (e.g., touch screen); (b) recording of a single-touch response to the sample by the subject on the recordation component (e.g., touch screen); (c) correlating the single-touch response to the sample and saving the response in a memory component; (d) repeating steps (a)-(c) for one or more additional samples. In some embodiments, the sample source comprises a microtiter plate. The invention is not limited by the number of samples or by the type of plate used to house the samples. For example, in some embodiments, the microtiter plate is a 6-, 8-, 12-, 16-, 24-, 32-, 48-, 64-, 96-, 384- or more well plate comprising 8, 16, 32, 64, 96 or more different samples. In some embodiments, the sample is delivered by an automated pipette component (or other suitable sample delivery component). In some embodiments, the automated pipette component withdraws a sample from the sample source and delivers it directly to the mouth of a subject.

In some embodiments, the automated pipette component comprises a mobile arm, micropipette, and disposable tip. In some embodiments, the disposable tip is replaced or washed between the sample and each additional sample. In some embodiments, the mobile arm: (i) adopts a first position to place the disposable tip attached to the pipette in the appropriate position for withdrawing the sample from the sample source; and (ii) adopts a second position to place the disposable tip attached to the pipette in the appropriate position for delivering the sample to the subject. In some embodiments, the mobile arm (iii) adopts a third position to eject the disposable tip into a waste component. In some embodiments, the mobile arm repeats steps (i) through (iii) for additional samples. In some embodiments, the mobile arm adopts a position to wash the tip (e.g., so that it can be used for more than one sample (e.g., used continuously from trial to trial) prior to being ejected into a waste component).

In some embodiments, the recordation component (e.g., touch screen) comprises a response field, wherein a first dimension of the field corresponds to a first characteristic desired to be measured with regard to the sample (e.g., a first taste-testing characteristic) and a second dimension of the field corresponds to a second characteristic desired to be measured with regard to the sample (e.g., a second taste-testing characteristic). The invention is not limited by the type of taste testing characteristics measured. Indeed, any and all characteristics related to taste may be measured including, but not limited to, bitter, sweet, salty, umami, sour, watery, etc. Further characteristics may comprise any taste that can result from a constellation of tastes, spicy, minty, cool, metallic, chemesthetic, mouth-feel, appetitiveness, aversiveness, etc.

In some embodiments, the first taste-testing characteristic is palatability and the second taste-testing characteristic is taste quality. Palatability is the degree to which a person or animal likes what it tastes, ranging from appetitive to aversive. In operational terms, palatability can be quantified as some measure of the likelihood of ingestion. When a subject is trained, using the training methods described herein, a subject's response to a stimulus provides an objective measure of palatability, not influenced by the subjective opinions of the subject. Taste quality is the degree to which something tastes like something else (e.g., sucrose-likeness). Taste quality is a comparison between one taste stimulus and a second, often standard, taste stimulus that is recognizable or remembered from previous exposure (e.g., memory or from training). Operationally, taste quality can be quantified as the similarity or disparity between two or more taste stimuli. When a subject is trained, using the training methods described herein, a subject's response to a stimulus provides an objective measure of taste quality, not influenced by the subjective opinions of the subject. In some embodiments, a single-touch response to a sample (e.g., on a touch screen display or grid) indicates both a first dimension and second dimension response to the sample. For example, in some embodiments, the single-touch response indicates the subject's response to the palatability and taste quality of the sample.

In another embodiment, the present invention provides methods of measuring objective responses from a subject to a test stimulus (e.g., a test compound or sample) comprising: (a) providing a control stimulus (e.g., a control compound or sample) to a subject; (b) recording a single-touch response to the control stimulus by the subject on a multi-dimensional (e.g., 2, 3 or more dimensional) response field, wherein each dimension represents a different characteristic of the test stimulus (e.g., a test compound or sample); (c) rewarding the subject if the single-touch response accurately (or lesser reward for nearly accurately) identified a correct response to the control stimulus; and (d) repeating steps (a)-(c) with additional control stimuli until the subject has been trained to consistently provide the correct single-touch response to control stimuli that vary in the different characteristics of the test stimulus (e.g., a test compound or sample). In some embodiments, the method further comprises (e) providing a test stimulus to the human subject; (f) recording a single-touch response to the test stimulus by the subject on the multi-dimensional response field; (g) correlating the response to the test stimulus; and (h) repeating steps (e)-(g) with additional test stimuli. In some embodiments, the single-touch response indicates independent scores for each characteristic. The invention is not limited by the characteristic of a test stimulus tested. Indeed, any type of characteristic of a test stimulus that can be perceived by a subject may be measured. In some embodiments, the test stimulus is a gustatory stimulus (e.g., a taste sample). In some embodiments, the different characteristics are palatability and taste quality. In other embodiments, characteristics such as bitter, sweet, salty, umami, sour, watery, or any novel taste that can result from a constellation of tastes, spicy, minty, cool, metallic, chemesthetic, mouth-feel, appetitiveness, aversiveness, palatability, and/or taste quality are tested and/or measured. In some embodiments, one or more of the control stimuli are selected from sucrose, quinine, NaCl, citric acid, licorice, and strevioside. The invention is not limited by the type of characteristics of a test stimulus measured utilizing the methods disclosed herein. For example, in some embodiments, the control stimuli are visual, auditory, tactile, and/or olfactory stimuli that are utilized in the methods disclosed herein to measure the visual, auditory, tactile, and/or olfactory characteristics of a test stimulus.

In some embodiments, the present invention provides devices for measuring objective responses from a subject to test stimuli comprising: (a) a sample presentation component that exposes a subject to a stimulus; and (b) a response field comprising a first dimension corresponding to a first characteristic of the stimulus and a second dimension corresponding to a second characteristic of the stimulus, wherein the subject uses a single touch on the response field to indicate a response to the stimulus. In some embodiments, the response field is presented on a touch screen. In some embodiments, the touch screen displays a recordation grid. In some embodiments, the device further comprises a processor component and a memory component. In some embodiments, the processor directs the sample presentation component to obtain the sample and deliver the sample to the subject. In some embodiments, the sample is obtained from the memory component or a physical sample source. In some embodiments, the processor identifies contact of the response filed by the subject as a response. In some embodiments, the response is recorded in the memory and correlated to the sample. In some embodiments, the device further comprises wireless sending and receiving capabilities that transmits responses over a wireless network to a remote storage component. Data present in a memory component and/or remote storage component may be accessed and analyzed at any time after measuring responses has been completed.

In some embodiments, any number of samples (e.g., of appropriate size and/or volume) are provided by any appropriate mechanism. Mechanisms of sample are not limited to automated pipettes. Delivery components may comprise automated or manual components. In some embodiments, a delivery component comprises a pipette, straw, tube, cup, plate (e.g., for solid samples) syringe, vial, card (e.g., for scent samples), etc. A delivery component may be stationary or dynamic (e.g., automated or manual movement).

In some embodiments, methods of testing are provided with multiple rounds of assessment. For example, a subject is exposed to a stimulus in a first round of testing and based on the subject's objective response to one or more characteristics of the sample, the sample is advanced to a subsequent round of testing. For example, a subject may be exposed to a sample (e.g., tastes it) and responds (e.g., on x/y axis) according to one or more characteristics (e.g., taste quality and palatability). In some embodiments, the response reflects a behavioral or sensory relationship not the subjective opinion of the subject. If one or more of the characteristics exceeds a threshold, the stimulus will move on to another round of testing. In other embodiments, a subject may be exposed to a sample (e.g., tastes it) and provide or emit a positive (e.g., 'yes', or 'advance') or negative (e.g., 'no' or 'reject') response according to one or more characteristics. In certain embodiments, a subject is exposed to a sample (e.g., tastes it) and the subject provides or emits a positive (e.g., 'yes', or 'advance') or negative (e.g., 'no' or 'reject') response according to one or more characteristics, which results in ranking the sample (e.g., on x/y axis) according to one or more characteristics; such a testing round is a combined assessment.

In some embodiments, a sample is assessed in a single round. One or more (e.g., 2, 3, 4, 5, 6, 7, 8, or more characteristics may be assessed per round. In some embodiments, a sample is assessed over multiple testing rounds. For example, based on the feedback from a subject or subjects, a sample is (1) discarded, or (2) advanced to an additional round of testing. In some embodiments, assessments of a sample are saved whether a sample is advanced or discarded. In certain embodiments, in a single round (e.g., based on a single exposure to a sample), a sample is assessed according to a subject's training for a first characteristic (e.g., taste quality), and an advancement decision (e.g., 1/0, yes/no, +/−, etc.) is provided according to a second characteristic (e.g., of palatability). In some embodiments, based on one or more assessments per round of testing the sample is advanced to an additional round.

In some embodiments, multiple rounds of testing are performed to assess the characteristics of a sample. Each round may be performed by the same or different subjects. In each round, the sample(s) may be assessed according to the same (e.g., taste quality and palatability) or different (e.g., flavor, palatability, sweetness, taste quality, etc.) characteristics. In some embodiments, the same subject performs multiple rounds of testing (e.g., multiple evaluations). In other embodiments, sample(s are evaluated using a first subject in one round, and then samples advanced for additional testing are evaluated using subsequent subjects (e.g., according to the same or different criteria). Single-subject testing, multiple-subject testing, or combinations thereof may be utilized.

In some embodiments, an assessment of a single sample is obtained using a single subject. In other embodiments, a subject assesses multiple samples in a single round of testing (e.g., 2, 5, 10, 15, 20, 25, 30, 40, 50, 60, 70, 80, 90, 100, 110, 120, 130, 140, 150, 160, 170, 180, 190, 200, 250, 300, 400, 500, and values and ranges therein). In some embodiments, a subject only performs a single round of testing. In some embodiments, a subject performed multiple rounds (e.g., 2, 3, 4, 5, 6, 7, 8, or more) of testing. In some embodiments, all samples are tested in each round. In other embodiments, some samples are discarded (e.g., based on objective assessment) in each round, leaving fewer samples in successive rounds.

In some embodiments, multiple subjects (e.g., 2, 5, 10, 20, 50, 100, 200, 500, 1000, or ranges therein) objectively assess a sample in a first round; and based on an average, combined, or otherwise collective score, the sample is rejected, accepted, and/or passed to a subsequent round of testing. In some embodiments, multiple subjects assess multiple samples; in such embodiments, based on an average, combined, or otherwise collective assessment, a portion of the samples are rejected and a portion of the samples are accepted or passed on to an additional round of testing.

In some embodiments, a test consists of a single round of testing (e.g., one subject and one sample, one subject and multiple samples, multiple subjects and one sample, multiple subjects and multiple samples). In some embodiments, a test consists of multiple rounds of testing. In some embodiments, the same subjects assess each round. In some embodiments, different cohorts of subject asses each round.

In some embodiments, provided herein are methods of measuring objective responses from a human subject to test stimuli, comprising: (a) providing a test stimulus to the human subject; (b) recording a positive or negative assessment (e.g., an objective assessment based on the training methods described herein), according to the subject's assessment of a characteristic of the stimuli; (c) repeating steps (a)-(b) with additional test stimuli; (d) advancing test stimuli that received a positive assessment on to an additional round of testing. In some embodiments, each stimulus is also assessed according to at least a second characteristic. In some embodiments, the additional round of testing is performed by the same subject, a different subject, or multiple different subjects.

DEFINITIONS

Figure 1:
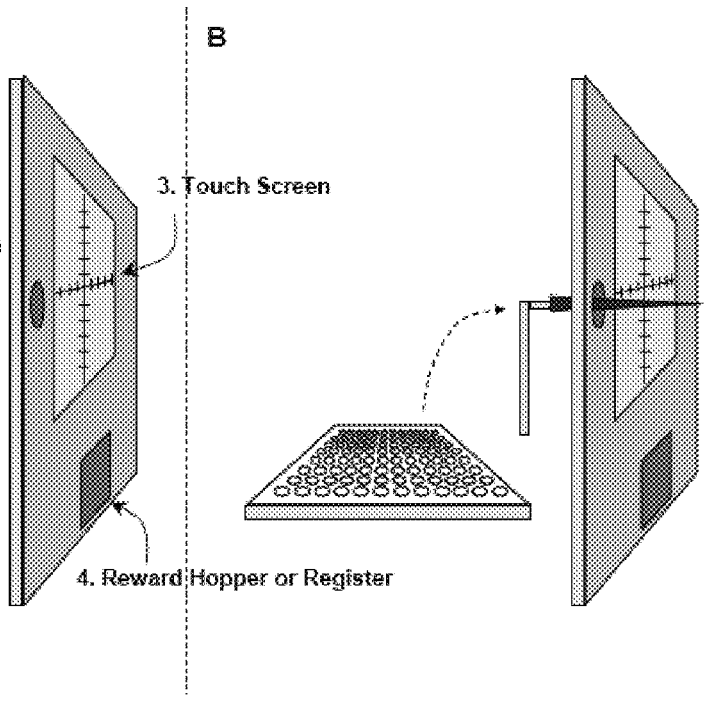
FIG. 1 shows a representation of an exemplary device of the invention comprising an automated pipette system 1, sample source plate 2, touch screen 3, and reward hopper or register 4: A: Pipette automatically draws sample (e.g., 100-300 µl) from a source plate (e.g., 96-well plate). B: The automated pipette presents the sample to a subject (e.g., through a port in the front panel of the workstation).

As used herein, the term "operant conditioning" refers to training or learning in which a subject's behavior is modified by its consequences. The response is initially spontaneous (e.g., touching a blank response grid after receiving a control sample, without prior instruction), but subsequent consequences (e.g., rewards or punishments (e.g., lack of reward)) reinforce or inhibit recurrence of that behavior, thereby teaching the subject how to properly respond. Responses to stimuli, based on operant conditioning, are objective responses, not biased by subjectivity of the respondent.

As used herein, the term "taste" refers to gustatory perception or sensation produced when a substance in the mouth reacts chemically with receptors of taste buds.

As used herein, the term "basic tastes" refer to the five tastes that human taste buds are able to differentiate among. The five basic tastes are typically referred to as sweetness, sourness, saltiness, bitterness, and umami.

A used herein, the term "flavor" refers to the sensory impression of a food or other ingestible substance (e.g., beverage, pharmaceutical, supplement, nutriceutical, etc.), and is determined primarily by the chemical senses of taste and smell. Temperature, texture, and irritant may also contribute to overall flavor perception.

As used herein, the term "taste quality" refers to the characteristic of a taste stimulus either being similar or different from a familiar taste. Taste quality is typically measured with respect to one basic taste. Comparisons to more complex tastes (e.g., chocolaty) may also be regarded as a function of taste quality. In more operational terms, taste quality is the result of the process of discrimination from or generalization to a control taste stimulus (e.g., similarity or difference from sucrose).

As used herein, the term "palatability" refers to the property of taste that determines how likable a substance is in the oral cavity (e.g., how good, or bad, does something taste). Palatability is a sensory characteristic closely associated with the nutritive value of food. For example, highly palatable foods and beverages often are calorie-dense, and as a result tend to be over-consumed. However, some non-caloric sweeteners used in diet drinks are considered to be highly palatable as well. Palatability can be operationally defined as the probability that a food or beverage will be consumed.

As used herein, the term "subjective" refers to a response that is based on the personal opinions, tastes, feelings, biases, etc. of a subject.

As used herein, the terms "objective" refers to a response representing observable facts, and not based on the personal opinions, tastes, feelings, biases, etc. of a subject.

DETAILED DESCRIPTION

Provided herein are methods of recording objective responses of a subject to stimuli, and devices and user interfaces (UI) for use therewith. In particular, the present invention provides UIs that allow a user to record objective multivariable responses to stimuli, devices comprising such UIs, and methods of using such UIs and devices to assess the characteristics of a sample or product.

In some embodiments, methods and systems are provided for obtaining objective responses from a human subject or subjects, based on stimuli. In some embodiments, the methods do not rely on a subject providing or describing his/her own subjective perception of the stimuli. Rather, a subject is trained using control stimuli to respond to a set (e.g., range) of stimuli with a corresponding set (e.g., range) of responses. For example, a subject is trained using control stimuli that reflect various values along a range for a particular characteristic; then, when a subject is given a test stimuli, the subject can accurately and objectively place the stimuli along the range for that characteristic (e.g., even if the subject has not been made aware of the identity of the particular characteristic). In some embodiments, the subject is not consciously aware of what characteristics he/she is responding to, but rather has been conditioned to objectively provide responses. After such training, when a test stimulus is provided, the subject's response is an objective assessment of the characteristic, based on the training, not biased by subjectivity. The subject's trained response is based on the subject's ability to discern and distinguish the characteristic(s) of the stimuli (a property of the subject's nervous system, not a reflection of the subject's judgment).

In certain embodiments, provided herein are methods of recording responses of subjects to gustatory stimuli (e.g., flavor stimuli), and devices and UI's for use therewith. In particular embodiments, UIs are provided that allow a subject (e.g., user, test subject) to record multivariable responses (e.g., taste quality and palatability) to received flavor stimuli (e.g., samples of varying sweetness, sourness, saltiness, bitterness, umami, etc.), devices comprising such UIs, and methods of using such UIs and devices to assess the flavor/taste/palatability of a product (e.g., ingestible product (e.g., food, beverage, flavoring, medicine, etc.)). For example, in some embodiments, the invention provides devices and methods to train a subject (e.g., by operant conditioning) to discriminate various characteristics (e.g., sweetness, sourness, bitterness, umami, palatability, tastiness, texture, etc.) of a taste-test stimulus (e.g., a test sample or compound). In particular embodiments, a subject rates (e.g., from low to high) the characteristics of the taste-test stimulus/sample. In particular embodiments, a subject rates (e.g., from low to high) the taste and palatability of the sample. In some embodiments, the subject is not aware of the characteristics being tested, but provides a response consistent with his/her training (e.g., operant conditioning). In some embodiments, the subject is aware of the characteristics being tested, but provides a response consistent with his/her training (e.g., operant conditioning).

However, the invention is not limited to measuring and testing characteristics of taste-test samples. Indeed, any type of characteristic of a test stimulus can be measured utilizing the devices and methods disclosed herein. For example, in some embodiments, visual, auditory, tactile, and/or olfactory characteristics of a test sample are measured utilizing the devices and methods disclosed herein.

Figure 2:
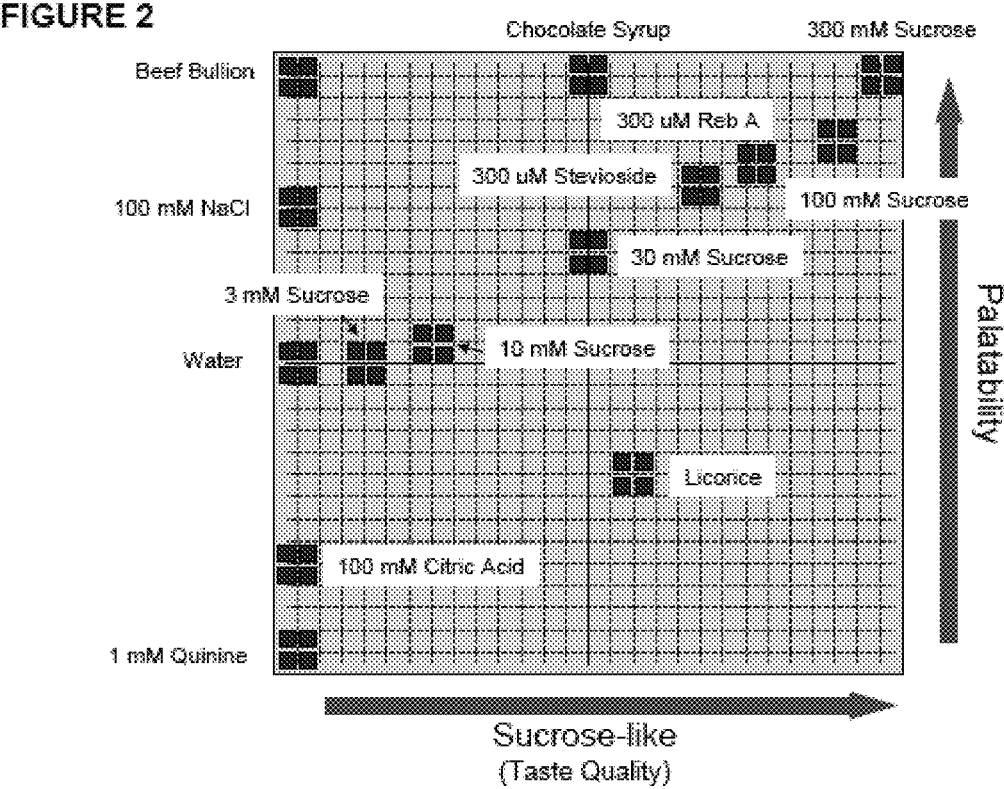
FIG. 2 shows a schematic of an exemplary touch screen of the invention showing response locations recorded for a single subject in a single hypothetical test in which a variety of samples have been evaluated for palatability and similarity to a standard of 100 mM Sucrose (e.g., taste quality). Responses to samples that range in palatability from neutral (represented by water) to highly palatable are in the top half of the screen and responses to unpalatable samples are in the lower half. Responses indicating similarity to sucrose taste appear in the right half, unlike sucrose in the left half of the screen. For example, licorice might be regarded as having some sweet characteristics, among other flavors, but overall regarded as unpalatable.

In some embodiments, samples are delivered to a subject in aliquots (e.g., less than 10 ml, less than 5 ml, less than 1 ml, less than 500 al, less than 200 al, 100-200 al, less than 100 µl). In some embodiments, samples are delivered to a subject by means of an automated pipette system or component (See, e.g., FIG. 1, element 1). Such small volumes (e.g., along with short sampling times) reduce the occurrence of desensitization. In some embodiments, a subject is capable of testing more samples than is conventionally possible due to the reduced sample volume being tested (e.g., increasing the speed or pace of sampling). In such embodiments, a pipette withdraws (or already contains) the aliquot (e.g., from a microtiter plate (e.g., 96-well plate, FIG. 1, element 2)) and automatically dispenses the sample for the subject (e.g., directly into the mouth of a subject). Upon receiving the sample, the subject records a response/reaction/impression on a UI of the invention. In some embodiments, the subject's responses are recorded on a touch screen with a grid (See, e.g., FIGS. 1 and 2, element 3; the grid may or may not be apparent to the subject). In some embodiments, the response pattern has two dimensions. In one embodiment of the invention, the measure of taste quality (or any other first characteristic) is recorded based on the location of the subject's touch in a range along the x-axis (e.g., with low taste quality (or perceived low level of first characteristic) represented by touches recorded on the far left (e.g., signifying highest degree of disparity to a taste standard) and high taste quality (or perceived high level of first characteristic) on the far right (e.g., signifying highest degree of similarity to a taste standard)). Likewise, palatability (or any other second characteristic) is recorded based on the location of the subject's touch in a range along the y-axis (e.g., with touches at the top of the screen signifying highest palatability (or perceived high level of second characteristic) and touches at the bottom of the screen signifying lowest palatability (or perceived low level of second characteristic)). In some embodiments, there is only one touch response per sample (e.g., constituting a single trial). Thus, according to one embodiment of the invention, a touch in the uppermost right-hand corner of the screen will indicate highest degree of similarity to the standard and maximal palatability, whereas touches in the lowermost left-hand corner are both maximally aversive and unlike the taste of the standard. In some embodiments, the response pattern can range along either or both axes to indicate varying degrees of similarity and palatability.

Methods and devices described herein present multiple advantages over conventional sample testing. For example, a trial with a single subject can be used to test many samples (e.g., >10 . . . >20 . . . >30 . . . >40 . . . >50 . . . >60 . . . >70 . . . >80 . . . >90 . . . >100 . . . >110 . . . >120 . . . >130 . . . >140 . . . >150 . . . >200, or more). In some embodiments, increased rapidity of sampling and/or reduced volume of samples allows for increase in number of samples and/or decreased time for trial. In some embodiments, fewer subjects are required for testing because a single subject can test more samples using the methods described herein.

In some embodiments, a reward system makes testing more enjoyable for the subject allowing them to reasonably continue testing more samples and/or for a longer duration. In some embodiments, "gamification" of the test is achieved, for example, through a weighted-reward strategy in which rewards are differentiated by quality of response. The degree of accuracy in performing a specific response is awarded with symbols or icons representing different values (e.g., points, achievement badges, advancement through a progression of levels of skill, virtual currency, or actual commodities of differing values, such as money). Additionally, in certain embodiments, the subject engages the test through an account with a self-chosen username and password, or avatar. In some embodiments, rewards for responses during the training phase and during the testing phase (e.g., for test samples or control samples) are varied according to the precision/accuracy of the response. In certain embodiments, auto shaping is used to vary the requirements for an acceptable answer as the trial progresses (e.g., monitored by responses to control samples during the testing phase). In some embodiments, rewards decrease or increase in magnitude or attractiveness as the subject's performance (monitored by control samples during the training or testing phase) declines or improves.

In some embodiments, the devices and methods described herein provide one or more of automated, high-throughput, statistically significant, objective, data-driven, mobile testing. For example, using a device and methods of the invention, a subject is able to evaluate a large number of different samples (e.g., 10, 15, 20, 25, 30, 35, 40, 45, 50, 75, 100 or more) different samples in a relatively short period of time (e.g., approximately 1-5 minutes or less, 5-10 minutes, 10-20 minutes, 20-30 minutes, 30-40 minutes, 30-50 minutes, 30-60 minutes, or 60-90 minutes). For example, utilizing devices and methods of the invention, a subject can evaluate 20 different samples in approximately 5 minutes or less, or 100 samples in 30 to 60 minutes or less.

Thus, the present invention makes possible the generation of relatively large datasets using only one, two or a few subjects for a particular analysis (e.g., taste analysis) that have heretofore not been possible. For example, conventional screens (e.g., taste tests) with human subjects has traditionally required relatively large numbers of subjects (e.g., 20-60) and only one, two, or a few different samples are able to be evaluated in a test. Thus, in some embodiments, the devices and methods of the invention are utilized for screening (e.g., primary screening) of libraries of samples (e.g., chemical or natural product libraries (e.g., for taste activity (e.g., by human subjects))) that have heretofore remained unavailable or unachievable.

Datasets generated utilizing the devices and methods of the invention allow predictive model building (e.g., of taste function) through curve-fitting analyses. For example, non-linear regression can be used to mathematically and rigorously define the relationship, for example, between concentration of a taste stimulus and the taste sensation evoked in a subject (e.g., tested and recorded utilizing the devices and methods described herein). The large, chemosensory datasets made available utilizing the devices and methods disclosed herein may be utilized for trend analyses (e.g., by linear, nonlinear, multivariate, simple, Bayseian, least squares, or polynomial regression) that predict future performance (e.g., of taste-based products) in larger groups or in the marketplace. These capabilities are not available or not achievable with conventional methods (e.g., of taste measurement), which require large numbers of subjects that evaluate only one, two or a few different samples per test. Because of the low throughput of data collection, the heretofore available conventional taste tests are dependent on statistical hypothesis-testing (e.g., ANOVA, Chi-squared tests, t-tests, or any non-parametric tests such as Kruskal-Wallis ANOVA, Mann-Whitney U, Wilcoxon Rank Sum, or Cohen's Kappa tests). In further embodiments, devices and methods of the invention make possible the tracking and recording of the responsiveness (e.g., taste responsiveness) of individual subjects over a period of time (e.g., over hours, days, weeks, months or years).

In certain embodiments, the methods and device of the invention reduce the number of subjects conventionally required for sample testing. In some embodiments, the number of subject is the same as conventional testing, but the number of data points is increased. The methods and devices allow the testing to be analyzed in an objective, data-driven manner. For example, devices and methods of the invention make possible few subjects (e.g., 1-10, 2-8, 3-4, etc.) generating many data points (e.g., 100-1000) instead of many subjects (e.g., 20-60) generating relatively few data points (e.g., 40-120). The present invention therefore makes available large sets of data (e.g., large data sets (e.g., with consistency among the sets due to the data being generated from a relatively small set of subjects)) that are amenable to regression analysis (e.g., predictive modeling, Bayesian statistics, etc. for example, by linear, nonlinear, multivariate, simple, Bayseian, least squares, or polynomial regression.)

For control trials, the subject receives a reward (e.g., money or other tangible good) for "correct" responses (e.g., those that are within a certain range of the expected response). A "correct" response in a sweet taste discrimination, for example, would be on the far right side near the top of the screen after a trial of 300 mM sucrose (e.g., high taste quality and high palatability), whereas a correct response for quinine would be in the lower left-hand corner (e.g., low taste quality and low palatability). In some embodiments, a reward will be automatically dispensed by means of an automated hopper within easy visual detection by the subject (See, e.g., FIG. 1, element 4). Alternatively, in some embodiments, a representative system, such as a point tally (or other symbol or means of translating value) provides reward for "correct" answers. In certain embodiments, the subject understands that a high point tally will translate to remuneration at the close of the test session. In some embodiments, a user can track success (e.g., visually).

The present invention makes possible conducting trials in which human subjects record their responses (e.g., multi-variable responses) to taste stimuli by touching a UI (e.g., touch screen). In some embodiments, subjects are told to touch anywhere on the screen, and are not informed of the contingencies for reward, the maximal number of trials, or a specified trial or session duration. In other embodiments, subject are instructed as to one or more of the contingencies for reward, the maximal number of trials, specified trial or session duration, etc. In some embodiments, all or a portion of a training session is conducted by operant conditioning. In some embodiments, all or a portion of a training session proceeds by successive approximation. For example, the subject is initially rewarded for responses to standard positive controls (e.g., sucrose, water, and/or quinine, citric acid, NaCl, glutamate, capsaicin, mustard oil, oleocanthal, menthol) that are made in a correct quadrant of a UI, then subsequently only in the correct portion of the quadrants, then subsequently only within a specified spot for each control in their respective quadrants. Once the response patterns for the controls satisfy a determined criterion (e.g., suitable accuracy and/or precision), then additional taste controls and/or test samples are incorporated into the trial. In some embodiments, additional controls (e.g., sucrose, water, and/or quinine, citric acid, NaCl, glutamate, capsaicin, mustard oil, oleocanthal, menthol) are utilized, with rewards, to refine a subject's ability to accurately respond to known or control samples. The invention provides a UI in which responses to specific controls will distribute along the x and y axes in a manner that is reproducible and consistent between users (e.g., if sucrose is used as a standard discriminatory cue, responses to water, quinine and NaCl will distribute along a far left y-axis, and sucrose responses will occur in the upper right-hand corner of the touch screen (See, e.g., FIG. 2)).

The devices and methods of the invention are configured, in some embodiments, such that during training sessions only "correct" responses are rewarded, whereas during test sessions, any response made during a trial with a test sample will be rewarded. In some embodiments, a goal of this method is to establish a rule for responding without verbal instruction from the test operator. Under these conditions, the subject will gain only a probabilistic comprehension of a rule or rules that could dictate the reward contingencies. Under such conditions, subjects may find themselves guessing the rules but will never know them with certainty. In some embodiments, additional control samples are administered (e.g., periodically, randomly, etc.) during testing phase to ensure continued accuracy and/or precision of responses (e.g., maintenance of operate conditioning). In some embodiments, rewards for testing-phase control samples are only given for "correct" responses. In some embodiments, failure to provide a correct response for one or more (e.g., successive) testing-phase control samples results in one or more of cessation of testing, return to training phase, or flagging of the trial. In other embodiments, failure to make a correct response for a control results in no reward on that trial. In still further embodiments, failure to make a correct response for a control results in a point (or other symbol or means of translating value) being removed from the subject (e.g., from the subjects total accrued value or tally).

Although embodiments of the present invention find use in a wide range of testing situations (e.g., market research, product development, etc.), particular embodiments related to high throughput testing of subject reactions (e.g., taste quality and palatability) to flavor stimuli have been described above and are highlighted throughout in greater detail herein. These embodiments should be viewed as exemplary, and the characteristics highlighted herein should be understood to apply to broader categories of testing (e.g., visual, auditory, tactile, and/or olfactory characteristics of a test stimulus/sample).

In some embodiments, subjects are trained to discriminate, for example, two or more characteristics of a sample. The samples are delivered to a subject under appropriate conditions to allow the subject to experience a reaction (e.g., gustatory, visual, auditory, tactile, olfactory). In some embodiments, a sample delivery component (e.g., pipette, video screen (e.g., depicting visual stimuli), hopper (e.g., containing a physical object), speaker, etc.) delivers the sample. In some embodiments, once the sample has been introduced to the subject, the subject enters a response to the sample on a user interface (e.g., GUI). In some embodiments, the UI is displayed on a touch-responsive screen. In certain embodiments, the UI comprises a multi-dimensional grid (See, e.g., FIGS. 1 and 2, element 3). In certain embodiments, the measure of a first characteristic is recorded by touching the screen in a range along the x-axis (e.g., low-degree of the first characteristic on the far left and high-degree of the first characteristic on the far right), and the measure of a second characteristic is recorded by touching the screen in a range along the y-axis (e.g., low-degree of the second characteristic on the far left and high-degree of the second characteristic on the far right). In such embodiments, a single touch on the grid indicates the user's response to the degree of the first and second characteristics of a sample. In some embodiments, there is only one touch to the UI per sample (constituting a single trial). In this embodiment, a touch in the uppermost right-hand corner of the screen indicates highest degree of both characteristics. Touches in the lowermost left-hand corner indicate the lowest degree of a characteristic. The response pattern can range along either or both axes to indicate varying degrees of the characteristics. The present invention is not limited to the above definitions for the UI. The range along the x-axis and/or y-axis can be defined in a suitable manner for the desired characteristic.

In some embodiments, subjects receive training in how to record responses. In some embodiments, known stimuli and/or control stimuli are provided and a subject's recorded responses thereto are used to calibrate the response field. In other embodiments, a subject is provided a control stimulus and then directed to the corresponding response on the UI. In some embodiments, a user is tested with control stimuli to ascertain whether a subject's test reactions are consistent with the training. In some embodiments, a subject is rewarded for consistent answers. In some embodiments, a subject is trained by operant conditioning. For example, the subject receives a sample and then reacts to the sample with a random reaction on the UI. If it is a "correct" response, the subject will receive a "reward." This training continues and the subject will learn how to respond to the control stimuli in order to receive the reward. In some embodiments, for control trials, the subject will receive a reward (e.g., money or other tangible good (e.g., a silver dollar)) for "correct"

responses. A correct response at judging the characteristics X and Y for control sample A might, for example, be on the far right side near the top of the screen (e.g., high in both characteristics X and Y), whereas a correct response for control sample B would be in the lower left-hand corner (e.g., low in both characteristics X and Y). In some embodiments, once a subject correctly responds to extreme test controls, like A and B above, more varied and moderate controls are tested. For example, a control sample that is low in characteristic X but moderate in characteristic Y would be correctly recorded by a touch on the far left, but in the middle vertically. In some embodiments, a subject is trained until the subject can consistently record accurate and precise answers to a variety of control samples (e.g., a predefined panel of control samples (e.g., high X and high Y, high X and low Y, low X and low Y, low X and high Y, moderate X and moderate Y, moderate X and high Y, moderate X and low Y, low X and moderate Y, high X and moderate Y, and intermediate samples there between). In some embodiments, precise and accurate responses are those within about 50% (e.g., <50%, <40%, <30%, <20%, <15%, <10%, <5%, <2%, <1%, etc.) of an axis distance from the correct location. Once a subject exhibits consistent ability to accurately and/or precisely respond to control stimuli, the training phase ends and the testing phase begins. In some embodiments, the subject is unaware of this transition.

In some embodiments, rather than training a subject, the device, user interface, software, or processor is 'trained' to understand a pattern to the subject's responses to control standards. The subject records responses to a series of control sample. The system is then calibrated according to those responses. In some embodiments, a subject may then be rewarded for accurate and precise responses according to the subject-calibrated scale. In certain embodiments, combinations of the above training methods are utilized. Modifications to these training methods are understood to be within the scope of the invention.

In some embodiments, once a subject has been trained to precisely and accurately record a response to a variety of control samples (e.g., a predefined panel), training ends and sample testing begins. The subject may or may not be informed of this transition. In some embodiments, all responses are rewarded for test samples. If a subject is properly trained in discriminating the tested characteristics, the subject's recorded answer provides an objective measure of those characteristics for the test sample. During testing, a subject is provided with a test sample and the subject records a reaction/impression to the ample on the UI, according to the rules 'learned' during training. In some embodiments, the user is unaware that training has ended, or that they ever underwent 'training.' In some embodiments, control samples are administered (e.g., periodically, randomly, etc.) during the testing phase as in-test controls. In certain embodiments, failure to provide "correct" responses to these in-test controls results in: test cessation, return to training, and/or flagging of the trial. In other embodiments, failure to make a correct response for a control results in no reward on that trial. In still further embodiments, failure to make a correct response for a control results in a point (or other symbol or means of translating value) being removed from the subject (e.g., from the subjects total accrued value or tally). In some embodiments, the subject is unaware that a control sample has been inaccurately responded to.

Characteristic (e.g., taste) testing may proceed by a variety of schemes within the scope of the methods described herein. For example, in some embodiments, a subject is in a test session in which multiple (dozens of) taste samples are being evaluated. Upon tasting a sample, a subject enters a response on a recordation component (e.g., touch screen) for taste quality. The subject subsequently registers a second response, which indicates the subject's desire to advance the sample tasted to an additional round of testing subsequent to the completion of the current testing. For example, the response indicates either "yes" or "no" for inclusion of the sample in a subsequent "bonus" round of testing. As an example 1 mM quinine would be followed by a "no" response and therefore is not advanced to the subsequent round; 300 mM sucrose is followed by a "yes" response and therefore is advanced to a subsequent round; samples that are not especially palatable, but also not especially aversive, could result in a "yes" on some trials and "no" on other trials (under the assumption that the same article is tested more than once during the test session.) Thus, a subject (or population) creates a secondary "plate" which reflects the palatability of the taste stimuli. Samples with the highest palatability will appear with the greatest frequency in the plate; samples will appear with decreasing frequency as palatability diminishes. In some embodiments, responses for test articles that are sampled once or only a few times within a single test session are averaged across subjects, or summated across subjects, to form the "bonus" plate. In some embodiments, multiple "bonus" rounds, in which samples are advanced across rounds, are implemented to further sort the samples according to palatability. Those samples with the greatest palatability advance the farthest (e.g., continue to be included in subsequent rounds), whereas those that are less palatable tend to drop out as the subject moves through subsequent "bonus" rounds. For example, 300 mM sucrose would advance all the way to a maximum of 10 "bonus" rounds, whereas 30 mM sucrose might only advance to the 5th round, not appearing in the plates for the 6th round and onward.

In one embodiment, systems and methods of the invention are utilized to identify a sample (e.g., among a sample set (e.g. tens, hundreds, thousands, tens of thousands or more)) that possesses certain characteristics (e.g., taste quality, palatability, or other taste characteristic identified herein). For example, in one non-limiting embodiment, the sample so identified (e.g., possessing a desired characteristic) is one that is objectively assessed and/or registered (e.g., by a user of a system and/or method of the invention) as being of high taste quality and/or palatability but that has a reduced amount of sugar compared to a control sample. In another non-limiting embodiment, the sample so identified (e.g., possessing a desired characteristic) is one that is objectively assessed and/or registered (e.g., by a user of a system and/or method of the invention) as being of high taste quality and/or palatability but that has a reduced amount of fat compared to a control sample.

In some embodiments, as an additional means for assessing a characteristic (e.g., palatability), the subject "pays" (using points accumulating during testing) for the samples that are to be included in the subsequent "bonus" rounds. Those with the greatest palatability would be expected to exact the most cost from the subject for inclusion in the "bonus" rounds, and as palatability diminishes so does the price the subject is willing to pay. The costs to the subject associated with creating a "bonus plate" are programmed to balance favorably with the incentives provided in the total point earnings for the game (e.g., the costs of making a new plate are less than the earnings incentives for continuing on to additional rounds of testing). Since aversive taste stimuli tend to disappear from subsequent "bonus" rounds, in some embodiments, the rules associating taste stimuli to regions of interest in the touch screen filed are adjusted for the additional rounds. In some embodiments, the rules change each round, and multiple rounds create "bonus plates" that contain only highly palatable taste stimuli (and thus a more limited selection of taste stimuli to use for establishing taste-designated regions of interest.) In some embodiments, the rules for each round change in such a way as to retain attention of the subject on game performance and away from conscious, subjective evaluation of the taste stimuli. The objective measure of taste remains a matter of the stimulus control over the accuracy and rate of the subject's performance in the task.

In other embodiments, the subject's quantitative ranking of a sample or stimuli objectively obtained from the subject's performance, behavior, or actions is utilized in advancing samples to subsequent rounds. In yet other embodiments, only a single round of testing it utilized.

In some embodiments, a UI is provided for recording the reaction, response, interpretation, etc. of a subject (e.g., human subject) to stimuli. In some embodiments, the UI allows the subject to record their reaction, response, interpretation, etc. by a single action (e.g., voice, contact with the UI, etc.). In some embodiments, in addition to the actual response, the time required for responding is also recorded. In particular embodiments, the UI provides a field (e.g., grid, axis, etc.) for the user to contact to indicate a reaction, response, interpretation, etc. to a sample. In some embodiments, only a single contact of the UI by the subject is needed for recordation. In certain embodiments, multi-variable (e.g., 2, 3, 4, 5, 6, 7, 8 or more) responses are recorded by a single touch of the UI. In other embodiments, multiple touches might be used to record multi-variable (e.g., 2, 3, 4, 5, 6, 7, 8 or more) responses. In some embodiments, a single touch of the response field by the subject records a three-variable response. In such embodiments, the response field comprises an x-axis representing a first variable a y-axis representing a second variable and a z-axis representing a third variable. In particular embodiments, a single touch of the response field by the subject records a two-variable response. In such embodiments, the response field comprises an x-axis representing a first variable and a y-axis representing a second variable. The location of a subjects contact with the field, relative to the x-axis and y-axis indicates the subjects rating of those two variables (e.g., high x and low y; high x and high y, moderate x and high y, low x, moderate y). In some embodiments, the two or more variables are related (e.g., same category of stimuli (e.g., visual, auditory, tactile, olfactory, gustatory), one variable is dependent upon the other (or anticipated by testers to be dependent upon the other), etc.). In some embodiments, the two or more variables are not directly related (e.g., different categories of stimuli (e.g., visual, auditory, tactile, olfactory, gustatory), variables are independent of each the other (or assessed by testers to be independent of each other). In some embodiments, a user will record reactions to multiple successive stimuli on the UI. In certain embodiments, each touch of the UI field by the subject records a reaction/impression to a successive stimulus.

In some embodiments, the present invention provides one or more user interfaces that allow interaction of the subject with one or more components of a device or system administering the training/testing. The primary UI provides a field for the subject to record responses. The present invention is not limited by the technology for displaying the UI or the configuration of the UI. In some embodiments, a UI is an electronic touch screen that detects the location of a subject's contact during a recordation mode. In other embodiments, an electronic touch UI may be accessed by a mouse, stylus, keyboard, etc. In some embodiments, the UI is not electronic, but records the physical contact of the subject's contact (e.g., carbon paper, marker on paper, etc.). In some embodiments, a UI is a graphical user interface. In some embodiments, a UI comprises a field upon which a subject's responses/impressions are recorded. In certain embodiments, the field allows for recording reaction to two variables with a single touch (e.g., two axis fields). In certain embodiments, the field allows for recording reaction to three variables with a single touch (e.g., three axis fields). In some embodiments, the field comprises a grid (e.g., invisible or apparent to a subject). In some embodiments, the location of subject contact on a multidimensional grid (e.g., 2, 3, 4, 5, or more dimensional grid) correlates to the reaction of the user to a sample. In some embodiments, the field comprises a grid and each square within the grid correlates to a different multi-variable response to the sample. In some embodiments, each axis of the grid may comprise individual segments. For example, the x-axis and y-axis of a grid may independently comprise, for example 2 segments, 3 segments, 4 segments, 5 segments, 6 segments, 7 segments, 8 segments, 9 segments, 10 segments, 15 segments, 20 segments, 25 segments, 30 segments, 40 segments, 50 segments, 60 segments, 70 segments, 80 segments, 90 segments, 100 segments, 200 segments, 500 segments, 1000 segments, or more. In some embodiments, a grid is 2×2, 2×3, 3×3, 4×4, 4×6, 5×5, 6×8, 8×10, 10×10, 10×15, 15×15, 20×20, 50×50, 100×100, 100×200, 500×1000, 1000×1000, or any sizes therein. In some embodiments, a grid or UI has a first and second dimension (e.g., height and width), independently selected from 4 cm . . . 6 cm . . . 8 cm . . . 10 cm . . . 15 cm . . . 20 cm . . . 25 cm . . . 30 cm . . . 35 cm . . . 40 cm . . . 45 cm . . . 50 cm, or more).

In some embodiments, a subject interacts with a first UI and an investigator or administrator monitors/administers the test from a second interface. In some embodiments, the investigator/administrator monitors/administers the tests of multiple subjects (e.g., 2 . . . 4 . . . 8 . . . 12 . . . 20, or more) using multiple devices (e.g., 1 per subject) from a single administrator UI.

In some embodiments, a subject response is recorded upon the initial contact of the subject to the screen. In other embodiments, the subject is allowed to adjust their response while maintaining a "mouse down" contact (e.g., finger on UI, mouse button depressed, etc). In such embodiments, a response is recorded at the location where the user ceases contact or goes "mouse up." In some embodiments, the subject indicates (e.g., with a separate action, touching a location on the UI, a button, etc.) when a final response has been recorded. In certain embodiments, a subject may indicated (e.g., with a separate action, touching a location on the UI, a button, etc.) when they wish to alter a response.

In some embodiments, a response UI is provided, along with one or more additional UIs. Other UIs that find use in embodiments may include on/off switches, pause buttons, next sample indicator, sample display components, sample administration components, etc.

In some embodiments, devices and/or systems are provided for administering the stimulus training/testing described herein. Devices may be specifically configured for carrying out the stimulus training/testing described herein, or may be more generic devices (e.g., computer, tablet, smartphone, etc.) that are utilized (e.g., with appropriate software or application) to perform the training/testing (e.g., by supplying a UI, by displaying/producing a stimulus, by recoding subject reactions, etc.). In some embodiments, a device or system comprises a UI. The UI may be en electronic field (e.g., screen (e.g., touch screen, video screen (interacted with via mouse or other component)), etc.) or analog field. In certain embodiments, the device displays the recordation field, and records the subject's interactions therewith. In some embodiments, a device or system comprises a component for holding/containing/storing/etc. stimuli or samples (e.g., microtiter plate (e.g., 96-well plate, 384-well plate, custom plate, etc.), computer memory (e.g., flash memory, CD/DVD, hard drive, etc.), etc. In some embodiments, the device or system comprises a component for providing/dispensing/displaying/etc. samples and/or stimuli (e.g., monitor, screen, hopper, pipette system (e.g., automated), etc.).

In some embodiments, a device comprises a microtiter operant gustometer coupled with a touch screen. In such embodiments, subjects (e.g., human subjects) are trained in taste discrimination by operant conditioning, and are then presented with a series of samples to rate according to one or more criteria (e.g., taste quality and palatability). A micropipette provides the subject with a sample (e.g., dispenses it (e.g., directly into a subject's mouth) and then the subject responds to the sample by contacting a 2D (x/y) field on the touch screen. The method captures the one or more (e.g., two) characteristics of the sample (e.g., taste quality and palatability) simultaneously for the sample. The micropipette is then cleaned or disposed of, and the testing process is repeated. As discussed herein, the 2D response field need not be a touch screen. Any component capable of registering a contact by a subject, and discerning the location of that contact relative to a 2D (x/y) grid is suitable (e.g., carbon paper, electronic pin grid, pen-on paper, etc.).

In some embodiments, following the subject's response the pipette tip will be ejected and replaced by a new pipette tip. Alternatively, the same tip will be retained but will be automatically rinsed with water. The pipette system then will return to the source plate to withdraw the next sample. A water rinse may also be automatically delivered to the subject in between each trial. The subject will perform this task until all samples have been evaluated (e.g., if a 96-well plate is the source of the tastant samples then a session will be comprised of 96 trials).

In some embodiments, software is provided to implement one or more steps of embodiments of the present invention. In some embodiments, software is provided that generates a UI for implementing the present invention on a generic device (e.g., touch-screen device (e.g., mobile phone, tablet, etc.)). In such embodiments, the software generates a UI touch field on the screen of a device. A subject indicates a reaction to stimuli marking a portion of the field (e.g., touching the screen, clicking a mouse at a location within the field, etc.). In some embodiments, software is provided that converts a generic device (e.g., the subject's own device (e.g., smartphone, tablet, etc.)) into a device for implementing embodiments of the present invention. In other embodiments, devices are provided that are specifically configured for carrying out the test methods described herein. Such devices comprise software elements that direct/facilitate various method steps (e.g., dispensing/providing stimuli, displaying UI field, recoding reactions, correlating/analyzing data, etc.).

In some embodiments, training and testing are performed at a testing facility and/or monitored/administered by a test monitor/administrator. In other embodiments, training and testing are performed by the subject, in the absence of monitoring/administration. In some embodiments, a device specifically designed to perform the training/testing is provided to the subject (along with appropriate samples), and the device administers the sample and record the responses appropriately (e.g., administering control samples in a manner to appropriately train the subject, switching from training to testing once the subject has provided sufficiently correct response). In some embodiments, training is administered according to an algorithm that guides the subject toward being test ready. In some embodiments, a subject is able to use his/her personal device (e.g., smart phone, personal computer, tablet, handheld device, etc.) to perform the test/training. In such embodiments, the subject is provided with the samples (e.g., actual physical samples, digital versions, etc.). In some embodiments, a software, program, application, etc. is installed on the subject's device to perform the training/testing. In some embodiments, the device instructs the subject on the order of samples, or provides the samples to the subject in the proper order. In some embodiments, the subject records responses on their own device.

In some embodiments, subject information (e.g., biographical information, age, sex, medications, known food allergies, etc.) is recorded and correlated with the results of the training/testing. In some embodiments, subject information is entered by the subject (e.g., at the UI). In other embodiments, an administrator enters the information. A subject may be issued (e.g., automatically) an ID number or username (e.g., to allow anonymity). In some embodiments, the ID and/or username are associated with data sets and/or test results.

In some embodiments, subject data sets are produced from the results of a trial (e.g., multiple samples tested by a single subject). In some embodiments, sample data sets are produced from the results on a single sample from multiple subjects. A data set may comprise the map coordinates for responses, time for response, normalized responses (e.g., normalized across the responses for a subject), trial number, subject ID, etc.

In some embodiments, the results of a test performed using the systems, devices and/or methods described herein (e.g., sensory test, test test, etc.) analysis are reported (e.g., to a subject, to the test administrator, researcher, principle investigator, etc.). Data (e.g., unmanipulated data) obtained from a subject may be reported as an outcome/result of a test. In other embodiments, data obtained from single subject is analyzed to provide output from interpretation, and it subsequently reported. Data from multiple subjects (e.g., having performed the same test or randomized versions of the same test) may be correlated and then analyzed and/or reported. Data and/or results may be produced by receiving data (e.g., from test of one or more subjects) and/or information (e.g., test samples, expected outcomes, desired outcomes, etc.), transforming the data and/or information and provide an outcome or result (e.g., by comparison to a database, by qualitative assessment, by quantitative assessment, etc.). A result obtained from correlation/analysis of test results may be determinative of an action to be taken (e.g., test different samples (e.g., variations of one or more tested samples), scale up the testing of a particular sample, commercialize a particular sample, etc.). In some embodiments, outcomes from testing by methods described herein are independently verified by further testing (e.g., larger scale testing, other testing strategies, etc.).

In some embodiments, results of testing (e.g., for a particular subject over a range of samples, for a single sample over a range of subjects, for a particular test, for a range of subjects and samples, etc.) are reported (e.g., to a: subject, test administrator, researcher, principle investigator, marketing team, management team, R&D team, etc.). In some embodiments, a result is provided on a peripheral, device, or component of an apparatus. For example, sometimes an outcome is provided by a printer or display. In some embodiments, results are reported in the form of a report. A report may reflect one or bother of quantitative and qualitative interpretation of results. Generally, results are displayed in a suitable format for downstream use/interpretation of the reported information. Non-limiting examples of formats suitable for use for reporting and/or displaying data, results, etc. include text, outline, digital data, a graph, graphs, a picture, a pictograph, a chart, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, and the like, and combinations of the foregoing.

Generating and reporting results from the tests described herein comprises transformation of subject (e.g., human subject) perceptions (e.g., sensory stimuli) into quantitative data (or representations thereof) that can be used for downstream evaluation of the samples tested. Such a data or representations reflect information not determinable from the individual subject's (or the population's) perception(s) in the absence of the method steps described herein. As such, in some embodiments, the method and systems provided herein address the problem of efficiently and objectively assessing characteristics of a sample (e.g., with reproducible or statistically significant accuracy/precision), particularly when such characteristics require human detection.

In some embodiments, a test administrator, researcher, principle investigator, or any downstream individual, upon receiving or reviewing a report comprising one or more data or results determined from the analyses provided herein, will take specific steps or actions in response. For example, testing of additional samples may be warranted. Production of additional samples may be ordered. Larger scale testing or testing by alternate means for one or more samples may be requested and/or performed. Commercial production of one or more samples may be initiated.

The term "receiving a report" as used herein refers to obtaining, by a communication means, a written and/or graphical representation comprising results or data from testing. The report may be generated by a computer or by human data entry, and can be communicated using electronic means (e.g., over the internet, via computer, via fax, from one network location to another location at the same or different physical sites), or by another method of sending or receiving data (e.g., mail service, courier service and the like). In some embodiments the outcome is transmitted in a suitable medium, including, without limitation, in verbal, document, or file form. Data, analysis, and/or reports may be encrypted to prevent unauthorized viewing. In some embodiments, data analysis, and/or reports are obtainable/viewable by a third party.

As noted above, in some embodiments, systems and method described herein transform data from one form into another form (e.g., subject assessment, population assessment, effect of an ingredient across different samples, effect of a change in ingredients (e.g., addition or an ingredient (e.g., natural or artificial alternative ingredient), etc.), etc. In some embodiments, the terms "transformed", "transformation", and grammatical derivations or equivalents thereof, refer to an alteration of data, e.g., from an initial assessment or set of assessments to a population response or determination regarding an input (e.g., a characteristic description of a sample across a population). In some embodiments, a transformation involves conversion of data comprising multiple assessments from a subject or subjects into a characteristic of a sample in order to solve a problem.

Certain processes and methods described herein (e.g., data acquisition, result analysis, communication, categorizing, database management, etc.) are performed by (or cannot be performed without) a computer, processor, software, module and/or other device. Methods described herein typically are computer-implemented methods, and one or more portions of a method sometimes are performed by one or more processors. In some embodiments, an automated method is embodied in software, processors, peripherals and/or an apparatus comprising the like, that administer or assist in the administration of testing, save data, perform analyses, make database comparisons, provide correlations, etc.

As used herein, software refers to computer readable program instructions that, when executed by a processor, perform computer operations, as described herein.

Apparatuses, devices, systems, software and interfaces may be used to conduct methods described herein. In some embodiments, such hardware and software components allow automation of one or more steps of the methods described herein. Using apparatuses, devices, systems, software and interfaces, a subject or test administrator may, for example, run a test on one or more (e.g., dozens, hundreds) of samples. In some embodiments, through automation, a test administrator may, for example, run a test on one or more (e.g., dozens, hundreds, etc.) of samples and multiple subjects (e.g., dozen, hundreds, etc.).

A system typically comprises one or more devices or apparatus. Each device/apparatus often comprises components selected from memory, processor(s), display, user interface, etc. Where a system includes two or more devices/apparatuses, some or all of the various components of the system may be located at different locations. Where a system includes two or more devices/apparatuses, some or all of the apparatus may be located at the same location as a user (e.g., subject, test administrator, etc), some or all of the apparatus may be located at a location different than a user, all of the apparatus may be located at the same location as the user, and/or all of the apparatus may be located at one or more locations different than the user.

A system may comprise one or more computing apparatuses (e.g., test-performing apparatuses, data analysis apparatus, database-containing apparatus, communication devices, reporting devices, etc.).

A user (e.g., test administrator, subject, etc.) of a device or method herein may, for example, be prompted by software to begin a test. The software/processor may prompt the user to take various steps (e.g., receive sample, score sample, etc.). A programmable processor also may prompt a user to select one or more options based on given parameters. A test administrator, principle investigator, or researcher may be provided (by software/hardware) with options for selecting one or more data feature selections, one or more statistical algorithms, one or more statistical analysis algorithms, one or more statistical significance algorithms, iterative steps, one or more validation algorithms, and one or more graphical representations.

Systems described herein may comprise general components of computer systems, such as, for example, network servers, laptop systems, desktop systems, handheld systems, personal digital assistants, tablets, smart phones, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

System components (e.g., individual testing units, recordation components (e.g. touch screen), etc.) may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user (e.g., subject, test administrator, researcher, principle investigator, etc.) accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, a suitable configuration and control may be utilized for mapping and/or processing data using multiple machines, such as in local network, remote network and/or "cloud" computing platforms.

A computer program product sometimes is embodied on a tangible computer-readable medium, and sometimes is tangibly embodied on a non-transitory computer-readable medium. A module sometimes is stored on a computer readable medium (e.g., disk, drive) or in memory (e.g., random access memory).

In some embodiments, systems described herein comprise or interact with a peripheral and/or component that provides data and/or information. In some embodiments, peripherals and components assist a system in carrying out a function. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., ipads, tablets), touch screens, smart phones, mobile phones, USB I/O devices, USB mass storage devices, keyboards, a computer mouse, digital pens, modems, hard drives, jump drives, flash drives, a processor, a server, CDs, DVDs, graphic cards, specialized I/O devices (e.g., photo cells, photo multiplier tubes, optical readers, sensors, etc.), one or more flow cells, solid material handling components, fluid handling components, network interface controllers, ROM, RAM, wireless transfer methods and devices (Bluetooth, WiFi, and the like), the world wide web (www), the internet, a computer and/or another module.

The terms "obtaining," "transferring," "receiving," etc. refer to movement of data (e.g., raw test data, processed date, taste signature, correlated data, combined data, population date, etc.) between modules, devices, apparatuses, etc. within a system. These terms may also refer to the handling of samples. Data may be generated in the same location at which it is received, or it may be generated in a different location and transmitted to the receiving location. In some embodiments, data is modified before it is processed (e.g., placed into a format amenable to processing, tabulated, correlated, combined, etc.).

Software may include one or more algorithms in certain embodiments. An algorithm may be used for processing sample, test, combined, and/or stored data; analyzing data; and/or providing results of one or more tests. An algorithm often is a list of defined instructions for completing a task. Starting from an initial state, the instructions may describe a computation that proceeds through a defined series of successive states, eventually terminating in a final ending state. By way of example, and without limitation, an algorithm may be a search algorithm, sorting algorithm, merge algorithm, numerical algorithm, graph algorithm, string algorithm, modeling algorithm, computational geometric algorithm, combinatorial algorithm, machine learning algorithm, cryptography algorithm, data compression algorithm, parsing algorithm and the like. In some embodiments, an algorithm or set of algorithms transform data (e.g., test data) into identifiable results. Algorithms utilized in embodiments herein make improvements in the fields of product design, product optimization, food science, marketing, etc. In certain embodiments, algorithms may be implemented for by software.

In some embodiments, systems and methods described herein solve problems in the design of new products (e.g., edible products), the optimization of products, and/or the alteration of products. Small changes made to a product (e.g., food, beverage, etc.) may make discernible changes to the human-perceived (e.g., consciously, subconsciously, etc.) characteristics of the product. Systems and methods allow researchers, manufacturers, product designers, etc. to assess how those small changes affect human perception of a product. For example, if a first sweetener (e.g., sugar, corn syrup, high fructose corn syrup, stevia, aspartame, sucralose, neotame, acesulfame, saccharin, etc.) in an established product is switched to a second sweetener (or the amount altered) the systems and methods described herein allow the human perception of that alteration (e.g., on palatability, on taste quality, etc.) to be assessed. Likewise, the effect on various characteristics (e.g., on palatability, on taste quality, etc.) of changes to the amount or type of any ingredient(s) (e.g., fat, salt, oil, spice, flavor, etc.) can be assessed by the systems and methods described herein. In some embodiments, methods and systems described herein find use in altering existing products according to consumer desires. For example, samples of an existing product are created with alteration of a particular ingredient and are tested for desirability to subjects (e.g., taste quality, palatability, etc.).

Any suitable product could be tested by embodiments described herein. Products that are particularly amenable are those that a user experiences and/or derives pleasure from, via taste and/or smell. Exemplary products include food items include processed foods such as beverages (e.g., drinks, sodas, sparkling waters, sweetened beverages, flavored beverages, etc.), snack foods (e.g., chips, crackers, cookies, etc.), etc. The effect of changes in fat content, salt content, sugar content, type of sweetener (e.g., natural v. artificial), etc. are assessed by methods and systems described herein.

EXPERIMENTAL

Example 1

Exemplary Training Module 1

Figure 3:
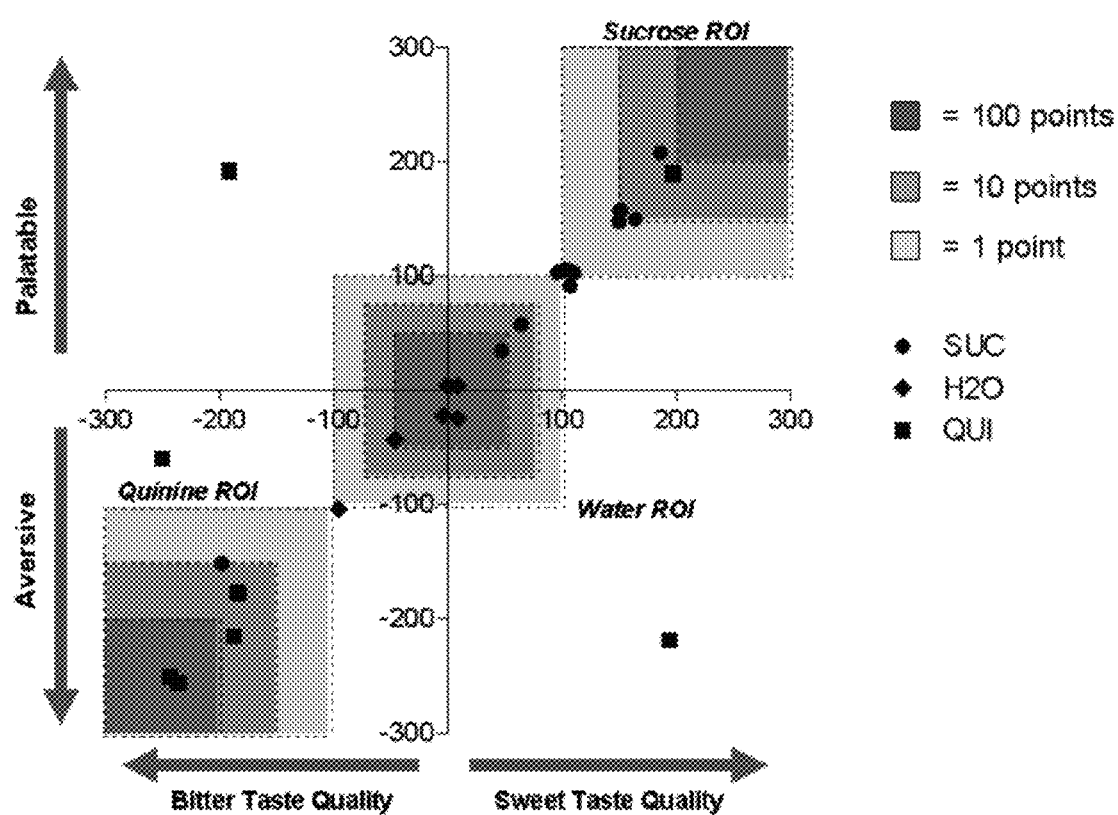
FIG. 3 shows a graph depicting results for a single subject (Subject 7) from an exemplary training module (Exemplary Training Module 1). Subject was instructed to find the point-carrying commodities within the field (a Cartesian grid) of a touch-sensitive monitor using taste stimuli as clues to locations. The regions of interest (ROIs) were programmed to be associated with the tastes of 100 mM sucrose (sweet), water (neutral), or 1 mM quinine (bitter). Concentric ROIs (different shades of gray) represent ranges of point values for responses made within the ROIs. Responses made outside of the ROIs resulted in a grayed-out screen, pause in play, and no points earned. Positive x-axis represents sweet taste quality, negative x-axis represents bitter taste quality. Positive y-axis represents palatable (appetitive) taste, negative y-axis represents aversive taste. Values on axes are pixels. Data points show locations of touch-responses made on the monitor following the subject's sampling of sucrose, water, or quinine. In this session, a total of 25 samples (200 µl volume each) were randomly presented to the subject.
Figure 4:
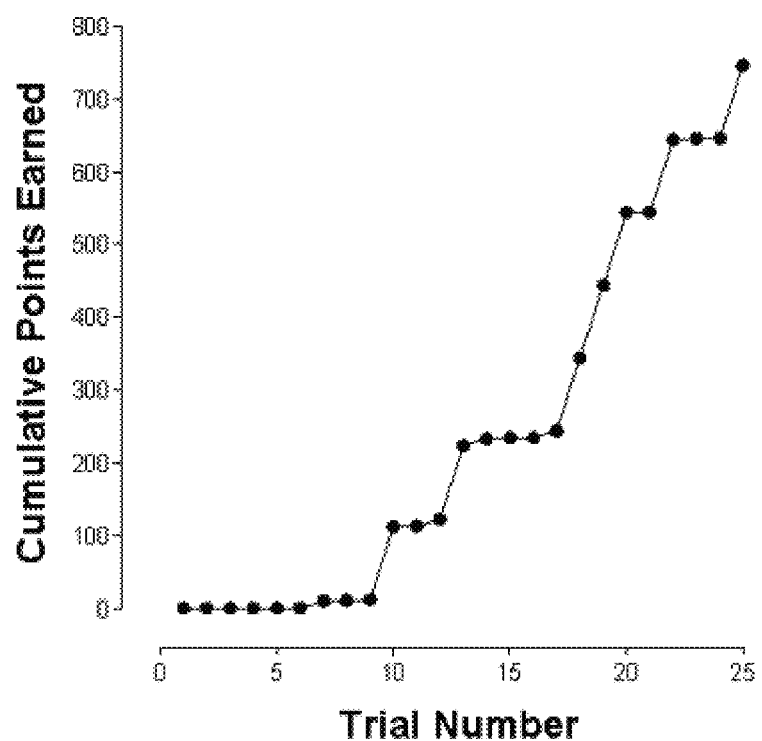
FIG. 4 show a graph depicting cumulative points earned by the subject (Subject 7) in an exemplary training module. Shown are the points accumulated per trial, with point increments of 1, 10, or 100. Points were cashed in at the end of the session for reimbursement at a rate of 1 cent per point.
Figure 5:
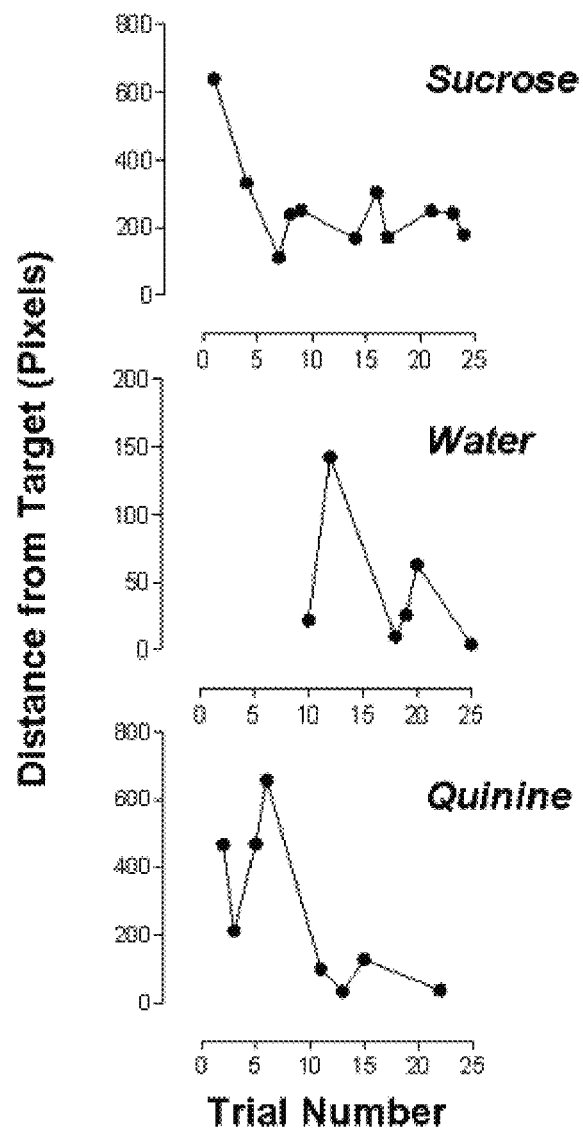
FIG. 5 shows graphs depicting the accuracy of a subject's (Subject 7) responses as a function of trial number in an exemplary training module. Accuracy was determined by measuring the distance from the x,y coordinates of the subject's response to those of the ideal target (in the center of the 100-point ROIs of FIG. 3). Distance was calculated using the Pythagorean equation, and each point in the graph represents the value of the distance in pixels on each trial.
Figure 6:
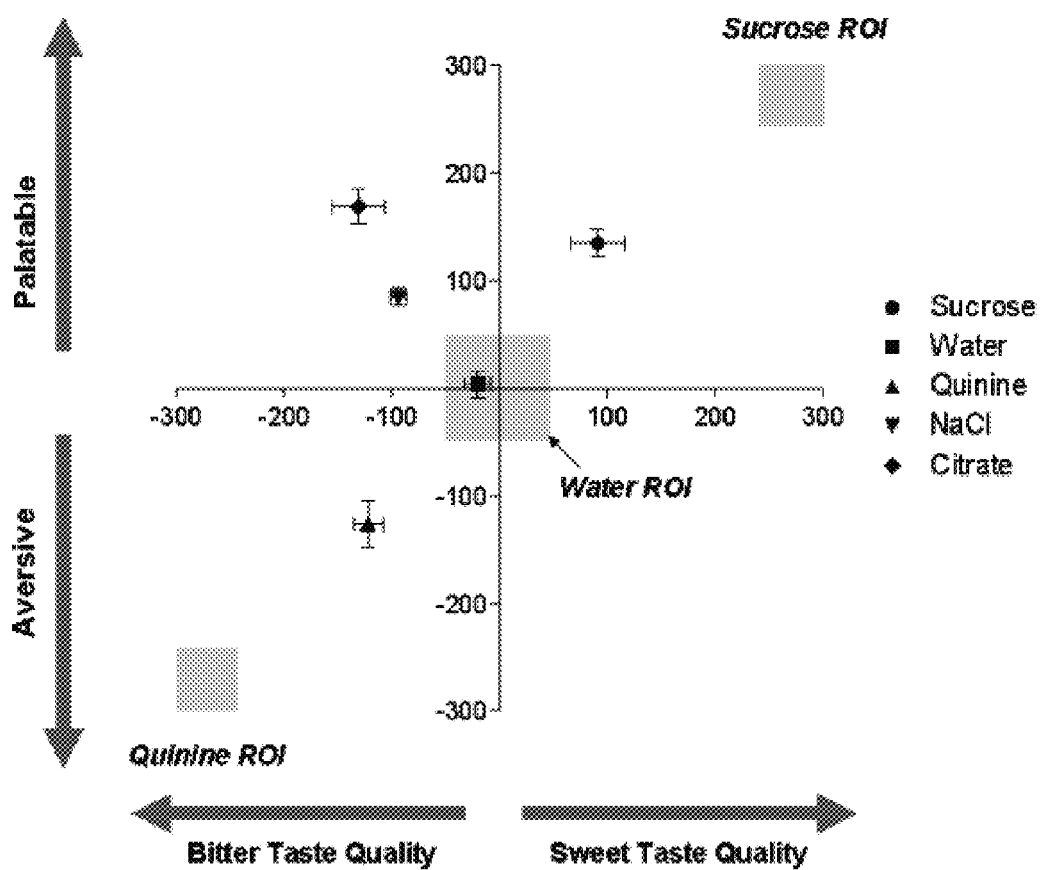
FIG. 6 shows a graph depicting results for a single subject (Subject 7) from an exemplary training module (Exemplary Training module 2). Conditions for training session were similar as those for the Exemplary Training Module 1, except that two additional taste stimuli, 100 mM NaCl (salty) and 10 mM citric acid (sour), were added as test articles-any response made in the left half of the field (i.e., any y point along the –x axis) following sampling of the salty or sour stimuli was rewarded with full value (100 points). NaCl was presented on 16 trials, and all other taste stimuli on 20 trials each, for a total of 96 trials. All samples were 200 µl volumes. Data shown are averaged results from Subject 7 in the first Training Module 2 session. Each point represents the averaged responses to each stimulus presented in random. Gray boxes in the figure represent the ROIs of highest point value for bitter, water, and sweet (as depicted in FIG. 3.)

Experiments were conducted during development of embodiments described herein in which subjects were instructed to find the point-carrying commodities within the field (a Cartesian grid) of a touch-sensitive monitor using taste stimuli as clues to locations. The regions of interest (ROIs) were programmed to be associated with the tastes of 100 mM sucrose (sweet), water (neutral), or 1 mM quinine (bitter). Successively larger concentric ROI around a primary region of interest represented areas of diminishing point value for responses made within the ROIs. Responses made outside of the ROIs resulted in a grayed-out screen, pause in play, and no points earned. On the Cartesian grid, positive x-axis represented sweet taste quality, negative x-axis represents bitter taste quality, positive y-axis represents palatable (appetitive) taste, and negative y-axis represents aversive taste; although the meaning of the axes were not disclosed to the subjects. Subjects were provided with a sample of sucrose, water, or quinine, and instructed to indicate a representative response on the monitor grid. Subjects were informed of their score for each response. In this session, a total of 25 samples (200 µl volume each) were randomly presented to each subject. FIG. 3 represents the results from Subject 7 during this training module; FIG. 4 represents the cumulative pointes earned by Subject 7 during the module; and FIG. 5 represents the distance of individual responses from the target, for each sample type.

Example 2

Exemplary Training Module 2

Additional experiments were conducted during development of embodiments described herein, utilizing the same format as above for Training Module 1, except that two additional taste stimuli, 100 mM NaCl (salty) and 10 mM citric acid (sour), were added as test articles—any response made in the left half of the field (i.e., any y point along the −x axis) following sampling of the salty or sour stimuli was rewarded with full value (100 points). NaCl was presented on 16 trials, and all other taste stimuli on 20 trials each, for a total of 96 trials. All samples were 200 µl volumes.

Responses to water were highly accurate, whereas responses to sucrose and quinine were less accurate (though within the "correct" quadrant). Subject 7's responses to the mildly salty and sour taste stimuli were not "shaped" by training, but did tend to occur in the non-sweet/palatable quadrant. This was an unexpected result, since responses made by the subject following sampling of the mildly sour and salty stimuli ended up in the non-sweet/palatable quadrant—the subject was rewarded for responses in the left half of the field (non-sweet taste quality) but there was no contingency for reward in the top half (appetitive palatability). The responses ended up there because they were unlike the aversive property trained by the association between lower half of the screen and quinine. Thus, the palatability of the NaCl and citric acid solutions was determined objectively. With continued training, Subject 7's responses are expected to shift toward greater accuracy but will stay within the respective quadrants determined in this session.

All publications and patents provided herein incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

The invention claimed is:

1. A device for human taste testing comprising:
   (a) a user interface comprising a touch screen, wherein the touch screen comprises a visible or invisible multidimensional response grid comprising a first dimension indicating a first taste-testing characteristic and a second dimension indicating a second taste-testing characteristic, wherein the response grid is configured to indicate, upon a single touch thereof, a level of the first and the second taste-testing characteristics present in a taste testing sample;
   (b) a source of human taste testing samples;
   (c) a processor component;
   (d) a memory component; and
   (e) an automated pipette component configured to withdraw a taste testing sample from the source of human taste testing samples and to deliver the taste testing sample to a subject;
   wherein the processor component is configured to record and to associate the single touch of the response grid with the taste testing sample.

2. The device of claim 1, wherein the first taste-testing characteristic is palatability and the second taste-testing characteristic is taste quality.

3. The device of claim 1, wherein the multidimensional response grid of the touch screen further comprises a third dimension indicating a third taste-testing characteristic and a fourth dimension indicating a fourth taste-testing characteristic.

4. The device of claim 3, wherein one or more of the first, second, third and/or fourth taste testing characteristics is selected from the group consisting of bitter, sweet, salty, umami, sour, spicy, minty, cool, metallic, chemesthetic, mouth-feel, appetitiveness, aversiveness, palatability, quality, and a combination of same.

5. The device of claim 1, wherein the processor component directs the automated pipette component to deliver a taste testing sample from the source of human taste testing samples to a subject.

6. The device of claim 1, further comprising a means for rewarding or a means for punishing a subject using the device.

7. A method of analyzing human taste test samples comprising:
   (a) providing a taste test sample to a human subject using a device for human taste testing comprising:
      (1) a user interface comprising a touch screen, wherein the touch screen comprises a visible or invisible multidimensional response grid comprising a first dimension indicating a first taste-testing characteristic and a second dimension indicating a second taste-testing characteristic, wherein the response grid is configured to indicate, upon a single touch thereof, a level of the first and the second taste-testing characteristics present in a taste testing sample;
      (2) a source of human taste testing samples;
      (3) a processor component;
      (4) a memory component; and
      (5) an automated pipette component configured to withdraw a taste testing sample from the source of human taste testing samples and to deliver the taste testing sample to a subject;
      wherein the processor component is configured to record and to associate the single touch of the response grid with the taste testing sample; and (b) the subject providing a single-touch response to the taste testing sample within the multidimensional response grid of the touch screen of the device.

8. The method of claim 7, wherein the subject's single-touch response is a result of operant conditioning.

9. The method of claim 8, wherein the subject is not aware of the taste-testing characteristic being analyzed.

10. The method of claim 7, wherein the subject's single-touch response is a multivariable response to the taste testing sample.

11. The method of claim 7, wherein the single-touch response indicates the level of a first taste-testing characteristic present in the taste testing sample, the level of a second taste-testing characteristic present in the taste testing sample, the level of a third taste-testing characteristic present in the taste testing sample, and/or the level of a fourth taste-testing characteristic present in the taste testing sample.

12. The method of claim 11, wherein one or more of the first, second, third, and/or fourth taste testing characteristic is selected from the group consisting of bitter, sweet, salty, umami, sour, spicy, minty, cool, metallic, chemesthetic, mouth-feel, appetitiveness, aversiveness, palatability, quality, and a combination of same.

13. The method of claim 7, further comprising step (c) the processor component recording the single-touch response to the taste testing sample and saving the response in the memory component of the device.

14. The method of claim 13, further comprising step (d) repeating steps (a)-(c) for one or more additional taste testing samples.

\* \* \* \* \*